United States Patent
Rout

(10) Patent No.: US 10,941,407 B2
(45) Date of Patent: *Mar. 9, 2021

(54) PLANT TRANSFORMATION WITHOUT SELECTION

(71) Applicant: MONSANTO TECHNOLOGY LLC, St. Louis, MO (US)

(72) Inventor: Jyoti R. Rout, Portland, OR (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,083

(22) Filed: Jan. 29, 2019

(65) Prior Publication Data

US 2019/0218562 A1 Jul. 18, 2019

Related U.S. Application Data

(60) Continuation of application No. 15/464,287, filed on Mar. 20, 2017, now Pat. No. 10,233,455, which is a division of application No. 14/494,495, filed on Sep. 23, 2014, now Pat. No. 9,617,552, which is a division of application No. 13/973,243, filed on Aug. 22, 2013, now Pat. No. 8,847,009, which is a continuation of application No. 11/848,579, filed on Aug. 31, 2007, now Pat. No. 8,581,035.

(60) Provisional application No. 60/841,519, filed on Aug. 31, 2006.

(51) Int. Cl.

| C12N 15/82 | (2006.01) |
|---|---|
| C12Q 1/68 | (2018.01) |
| C12Q 1/25 | (2006.01) |
| A01H 1/04 | (2006.01) |
| A01H 6/46 | (2018.01) |
| A01H 4/00 | (2006.01) |
| G01N 33/53 | (2006.01) |
| C12Q 1/686 | (2018.01) |
| C12Q 1/6813 | (2018.01) |

(52) U.S. Cl.
CPC ........... *C12N 15/8201* (2013.01); *A01H 1/04* (2013.01); *A01H 4/001* (2013.01); *A01H 6/4684* (2018.05); *C12N 15/821* (2013.01); *C12N 15/8209* (2013.01); *C12N 15/8212* (2013.01); *C12N 15/8265* (2013.01); *C12N 15/8205* (2013.01); *C12N 15/8261* (2013.01); *C12Q 1/25* (2013.01); *C12Q 1/686* (2013.01); *C12Q 1/6813* (2013.01); *G01N 33/53* (2013.01)

(58) Field of Classification Search
None
See application file for complete search history.

(56) References Cited

U.S. PATENT DOCUMENTS

| 3,847,888 | A | 11/1974 | Baumgaertner |
|---|---|---|---|
| 3,975,481 | A | 8/1976 | Baumgaertner |
| 5,164,310 | A | 11/1992 | Smith et al. |
| 5,177,010 | A | 1/1993 | Goldman et al. |
| 5,225,341 | A | 7/1993 | Yoder et al. |
| 5,349,124 | A | 9/1994 | Fischhoff et al. |
| 5,364,780 | A | 11/1994 | Hershey |
| 5,393,473 | A | 2/1995 | Payer et al. |
| 5,468,809 | A | 11/1995 | Ghisellini et al. |
| 5,484,620 | A | 1/1996 | Oechsle et al. |
| 5,547,481 | A | 8/1996 | Herding et al. |
| 5,767,368 | A | 6/1998 | Zhong et al. |
| 5,919,999 | A | 7/1999 | Ko et al. |
| 5,994,624 | A | 11/1999 | Trolinder et al. |
| 6,140,555 | A | 10/2000 | Reichert et al. |
| 6,265,638 | B1 | 7/2001 | Bidney et al. |
| 6,329,571 | B1 | 12/2001 | Hiei |
| 6,420,630 | B1 | 7/2002 | Wilson et al. |
| 6,825,397 | B1 | 11/2004 | Lowe |
| 7,682,829 | B2 | 3/2010 | Cai et al. |
| 7,939,325 | B2 | 5/2011 | Adams et al. |
| 8,124,411 | B2 | 2/2012 | Akula et al. |
| 8,357,836 | B2 | 1/2013 | Ishida et al. |
| 8,395,020 | B2 | 3/2013 | Rout et al. |
| 8,513,016 | B2 | 8/2013 | Akula et al. |
| 8,581,035 | B2 | 11/2013 | Rout et al. |
| 8,815,596 | B2 | 8/2014 | Adams et al. |
| 8,853,488 | B2 | 10/2014 | Rout et al. |
| 8,962,326 | B2 | 2/2015 | Akula et al. |
| 10,006,036 | B2 | 6/2018 | Akula et al. |
| 10,091,957 | B2 | 10/2018 | Adams et al. |
| 2003/0115641 | A1 | 6/2003 | Dobres et al. |
| 2004/0210959 | A1 | 10/2004 | Armstrong |

(Continued)

FOREIGN PATENT DOCUMENTS

| AU | 752717 B2 | 5/1999 |
|---|---|---|
| CA | 2087610 | 9/2000 |

(Continued)

OTHER PUBLICATIONS

U.S. Appl. No. 16/106,342, filed Aug. 21, 2018, Adams et al.
Chupeau et al., "Recovery of transgenic trees after electroporation of poplar protplasts," *Transgenic Res.*, 3(1):13-19, 1994.
Darbani et al., "Methods to produce marker-free transgenic plants," *Biotechnology J.*, 2:83-90, 2007.
Devetten et al., "A transformation method for obtaining marker-free plants of a cross-pollinating and vegetatively propagated crop," *Nature Biotechnology*, 21:439-442, 2003.

(Continued)

*Primary Examiner* — David T Fox
(74) *Attorney, Agent, or Firm* — Dentons US LLP; David Lanzotti, Esq.

(57) ABSTRACT

The invention provides methods for identifying regenerated transformed plants and differentiated transformed plant parts, obtained without subjecting plant cells to selective conditions prior to regenerating the cells to obtain differentiated tissues. In particular embodiments, the plant cells are corn plant cells. Methods for growing and handling plants, including identifying plants that demonstrate specific traits of interest are also provided.

8 Claims, 9 Drawing Sheets

(56) References Cited

U.S. PATENT DOCUMENTS

| | | |
|---|---|---|
| 2004/0210961 A1 | 10/2004 | Palys et al. |
| 2005/0097641 A1 | 5/2005 | Wolters et al. |
| 2018/0119157 A1 | 5/2018 | Rout et al. |
| 2018/0273959 A1 | 9/2018 | Akula et al. |

FOREIGN PATENT DOCUMENTS

| | | |
|---|---|---|
| CA | 2 401 954 A1 | 9/2001 |
| CA | 2 433 830 A1 | 7/2002 |
| CN | 1206435 A | 1/1999 |
| EP | 0 152 107 A2 | 8/1985 |
| EP | 0 159 418 A1 | 10/1985 |
| EP | 0 159 418 B1 | 5/1990 |
| EP | 0 429 093 B1 | 5/1991 |
| EP | 0 672 752 | 9/1995 |
| EP | 0 687 730 A1 | 12/1995 |
| EP | 0 897 013 | 2/1999 |
| EP | 0 904 908 A1 | 3/1999 |
| EP | 1 111 063 A1 | 6/2001 |
| EP | 2127517 A1 | 12/2009 |
| JP | 2011-120487 | 6/2011 |
| WO | WO 83/01176 A1 | 4/1983 |
| WO | WO 85/01856 A1 | 5/1985 |
| WO | WO 85/04365 A1 | 10/1985 |
| WO | WO 95/06127 | 3/1995 |
| WO | WO 95/06128 | 3/1995 |
| WO | WO 97/41228 | 11/1997 |
| WO | WO 98/51806 | 11/1998 |
| WO | WO 99/20776 A1 | 4/1999 |
| WO | WO 00/18939 A1 | 4/2000 |
| WO | WO 01/05936 A2 | 1/2001 |
| WO | WO 01/64023 A1 | 9/2001 |
| WO | WO 01/81330 A2 | 11/2001 |
| WO | WO 01/64023 B1 | 12/2001 |
| WO | WO 02/37951 | 5/2002 |
| WO | WO 02/055651 A2 | 7/2002 |
| WO | WO 02/102979 | 12/2002 |
| WO | WO 03/009673 A1 | 2/2003 |
| WO | WO 03/010319 A2 | 2/2003 |
| WO | WO 03/048369 A2 | 6/2003 |
| WO | WO 04/081184 | 9/2004 |
| WO | WO 2004/092390 | 10/2004 |
| WO | WO 2006/011959 | 2/2006 |
| WO | WO 2008/105509 | 9/2008 |
| WO | WO 2009/122962 | 10/2009 |

OTHER PUBLICATIONS

Espinosa et al., "Production of pineapple transgenic plants assisted by temporary immersion bioreactors," *Plant Cell Rep.*, 21:136-140, 2002.
Frame et al., "Agrobacterium tumefaciens-Mediated Transformation of Maize Embryos Using a Standard Binary Vector System", *Plant Physiol.* 129:13-22, 2002.
Francis et al., "Identification of *Arabidopsis thaliana* transformants without selection reveals a high occurrence of silenced T-DNA integrations," *The Plant J.*, 41:464-477, 2005.
Fraser, et al., "Application of high-performance liquid chromatography with photodiode array detection to the metabolic profiling of plant isoprenoids," *Plant J.*, 24:551-558, 2000.
Fromm et al., "Inheritance and expression of chimeric genes in the progeny of transgenic maize plants," *Bio/Technology*, 8:833-839, 1990.
Goldsbrough, "Unnecessary transgene integration and expression in plants: how do we minimise and manage this?" Department for Environment, Food & Rural Affairs, UK, www.defra.gov.uk/environment/acre/uti/08.htm., Feb. 16, 2001.
Graves et al., "The transformation of *Zea mays* seedlings with Agrobacterium tumefaciens", *Plant Mol. Biol.* 7:43-50, 1986.
Hood et al., "T-DNA and opine synthetic loci in tumors incited by agrobacterium tumefaciens A281 on soybean and alfalfa plants," *J. Bacteriol.*, 168:1283-1290, 1986.
Horikawa et al., "Transformants through Pollination of Mature Maize (*Zea may* L.) Pollen Delivered bar Gene by Particle Gun", *Grassland Sci.* 43:117-23, 1997.
Huang et al., "Generation of marker-free transgenic maize by regular two-border agrobacterium transformation vectors," *Transgenic Res.*, 13(5):451-461, 2004.
Jia et al., "Transformation of tomato with the BADH gene from atriplex improves salt tolerance," *Plant Cell Reports*, 21(2):141-146, 2002.
Kuipers et al., "Factors affecting the inhibition by antisense RNA of granule-bound starch synthase gene expression in potato," *Mol. Gen. Genet.*, 246:745-755, 1995.
Li et al., "Development of Protoporphyrinogen Oxidase as an Efficient Selection Marker for Agrobacterium tumefaciens-Mediated Transformation of Maize", *Plant Physiol.* 133:736-47, 2003.
Mtshali et al., "In vitro culture of sugarcane in a liquid temporary immersion system and assessment of potential use in transgenesis," 30$^{th}$ Annual Congress of the South African Association of Botanists, Durban, Sout Africa, Jan. 19-22, 2004.
Sairam et al., "Shoot meristem: an ideal explant for *Zea mays* L. transformation," *Genome*, 46:323-329, 2003.
Shaul et al., "Concerted regulation of lysine and threonine synthesis in tobacco plants expressing bacterial feedback-insensitive aspartate kinase and dihydrodipicolinate synthase," *Plant Mol. Biol.*, 23(4):759-768, 1993.
Sitbon et al., "Free and conjugated indoleacetic acid (IAA) contents in transgenic tobacco plants expressing the iaaM and iaaH IAA biosynthesis genes from agrobacterium tumefaciens," *Plant Physiol.*, 95:480-485, 1991.
Stam et al., "Distinct features of post-transcriptional gene silencing by antisense transgenes in single copy and inverted T-DNA repeat loci," *Plant J.*, 21(1):27-42, 2000.
Stam et al., "Review Article: The silence of genes in transgenic plants," *Annals of Botany*, 79(1):3-12, 1997.
Visser et al., "Inhibition of the expression of the gene for granule-bound starch synthase in potato by antisense constructs," *Mol. Gen. Genet.*, 225:289-296, 1991.
Zhao et al., "High throughput genetic transformation mediated by agrobacterium tumefaciens in maize," *Molecular Breeding*, 8:323-333, 2001.
Translation of Office Action dated Jan. 8, 2013, in Japanese Application No. JP 2009-526931.
English translation of office action dated Sep. 16, 2010, in Chinese Patent Application No. 200780040000.2.

PLANT TRANSFORMATION WITHOUT SELECTION

This application is a continuation of U.S. Ser. No. 15/464,287, filed Mar. 20, 2017, now U.S. Pat. No. 10,233,455, which is a continuation of U.S. Ser. No. 14/494,495, filed Sep. 23, 2014, now U.S. Pat. No. 9,617,552, which is a divisional of U.S. Ser. No. 13/973,243, filed Aug. 22, 2013; now U.S. Pat. No. 8,847,009, which is a continuation of U.S. Ser. No. 11/848,579, filed Aug. 31, 2007, now U.S. Pat. No. 8,581,035, which claims the priority of U.S. provisional application Ser. No. 60/841,519, filed Aug. 31, 2006, the entire disclosures of which are incorporated herein by reference in their entireties.

BACKGROUND OF THE INVENTION

1. Field of the Invention

The invention relates to the field of plant biotechnology. In particular, the invention relates to methods for producing transgenic plants not requiring use of a selectable marker gene prior to obtaining a regenerated plant or plant part.

2. Description of the Related Art

Stable transformation of plant cells and production of transgenic plants has typically required a selection step, wherein plant tissue is selected in the presence of a selection agent after having been contacted by one or more exogenous nucleic acid sequences, including ones that comprise a sequence or sequences encoding a gene of interest and a marker gene. Following such selection, stably transformed plants comprising a gene of interest (GOI) may be regenerated and identified. However, upon creating a transformed plant comprising a GOI, a selectable or screenable marker gene which is not itself a GOI is typically no longer necessary, and its presence may complicate subsequent analyses and product development efforts. Furthermore, the necessity of a strong promoter to drive a selectable marker has been shown to bias the expression of the desired gene (Yoo et al., 2005).

A wide range of methods has been reported for creating marker-gene free transgenic plants, for example co-transformation, transposable elements, site-specific recombination, and intrachromosomal recombination (e.g. Darbani et al., 2007). However most of these systems are time-consuming and inefficient. Goldsbrough (2001) reviews methods for avoiding the use of, or eliminating, selectable marker genes in creating transgenic plants.

De Vetten et al., (2003; and U.S. Patent Application Publication 2005/0097641) describe methods for marker-free transformation of a vegetatively propagated crop, such as potato, however resulting in chimeric plants. Palys et al. (PCT Publication WO 2004/081184) describe transformation of tomato, lettuce, and cabbage without selection. Francis and Spiker (2005) describe identification of transgenic *Arabidopsis* lines using a PCR-based screen, to avoid selection bias in transgene integration. In contrast, the present invention provides methods for rapid and efficient production of germline-transformed corn plants obtained via methods not requiring the presence of a selective agent or a screenable marker gene, such as a visual marker gene, prior to obtaining regenerated corn plants.

SUMMARY OF THE INVENTION

In one aspect, the invention provides a method for identifying transgenic corn plants, comprising: (a) obtaining corn plant cells transformed with a DNA segment comprising a nucleic acid sequence of interest; (b) regenerating a plurality of corn plants or differentiated corn plant parts from the cells without first selecting for the presence of said DNA segment; and (c) identifying at least a first transgenic corn plant or differentiated plant part from the plurality of corn plants or differentiated corn plant parts. In some embodiments, the DNA segment does not comprise a selectable marker gene, or a visual marker gene. In other embodiments, the plants are regenerated by growth on solid media, liquid media, or a combination of solid and liquid media. In particular embodiments, the plants are regenerated by growth solely on liquid media subsequent to contacting the cells with a GOI and prior to identifying the transgenic corn plant or transgenic differentiated plant part. In certain embodiments, the transformation frequency of cells grown solely in liquid media subsequent to contacting the cells with a GOI and prior to identification of transgenic plants or transgenic plant parts is enhanced relative to the transformation frequency observed when cells are grown in solid media or soil subsequent to contacting the cells with a GOI and prior to identification of transgenic plants or transgenic plant parts.

In certain embodiments, the plant cells are immature corn embryo cells. In particular embodiments the immature corn embryos are from about 1.5 mm to about 3.5 mm in length, or from about 1.9 mm to about 2.3 mm in length.

In certain embodiments, the method further comprises, between steps (b) and (c), (1) placing the plurality of corn plants or differentiated plant parts in culture tubes or growth plugs comprising a growth medium or water while maintaining the individual identity of the corn plants; and (2) subjecting the plants or plant parts to at least a first assay for the presence of the DNA segment to identify one or more plant or plant part as transgenic based on results from the assay. The assay may further be selected from the group consisting of Southern hybridization, PCR, DNA sequencing, northern blotting, western blotting, an immunoassay, and an assay for the enzymatic activity encoded by the DNA segment. In particular embodiments the assay is performed prior to placing the regenerated plants into soil. In other embodiments, the putatively transformed corn plants or differentiated plant parts lacking the nucleic acid sequence of interest are identified, wherein the assay is performed on plant tissue comprising pooled subsets of nucleic acids from said plurality of corn plants or differentiated plant parts.

In some embodiments, the corn plants or corn plant parts are regenerated not later than 6 weeks after the DNA segment is transformed into the corn plant cells. In other embodiments, the corn plants or corn plant parts are regenerated not later than 4 weeks after the DNA segment is transformed into the corn plant cells. In yet other embodiments, the corn plants or corn plant parts are regenerated not later than 3 weeks after the DNA segment is transformed into the corn plant cells. In still yet other embodiments, the corn plants or corn plant parts are regenerated not later than 2 weeks after the DNA segment is transformed into the corn plant cells. In further embodiments, the corn plants or corn plant parts are regenerated not later than 1 week after the DNA segment is transformed into the corn plant cells.

In certain embodiments, the DNA segment is introduced into the corn plant cell by bacterially-mediated transformation, electroporation, PEG-mediated transformation, or particle bombardment. In particular embodiments, the bacterially-mediated transformation is mediated by a bacterial cell selected from the group consisting of an *Agrobacterium* cell, a *Rhizobium* cell, a *Sinorhizobium* cell, and a *Mesorhizobium* cell.

The method may further comprise the step of subjecting a corn plant or plant part derived from the first corn plant cell to culture conditions that select for, or allow screening for, the presence or absence of the nucleic acid sequence of interest after regeneration of a plant or plant part. In certain embodiments, the growth medium is a solid medium. In yet other embodiments, the growth medium is liquid. In still other embodiments, the growth medium is soil. In other embodiments the regenerated plant or differentiated plant part is uniform with respect to the presence of the DNA segment.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
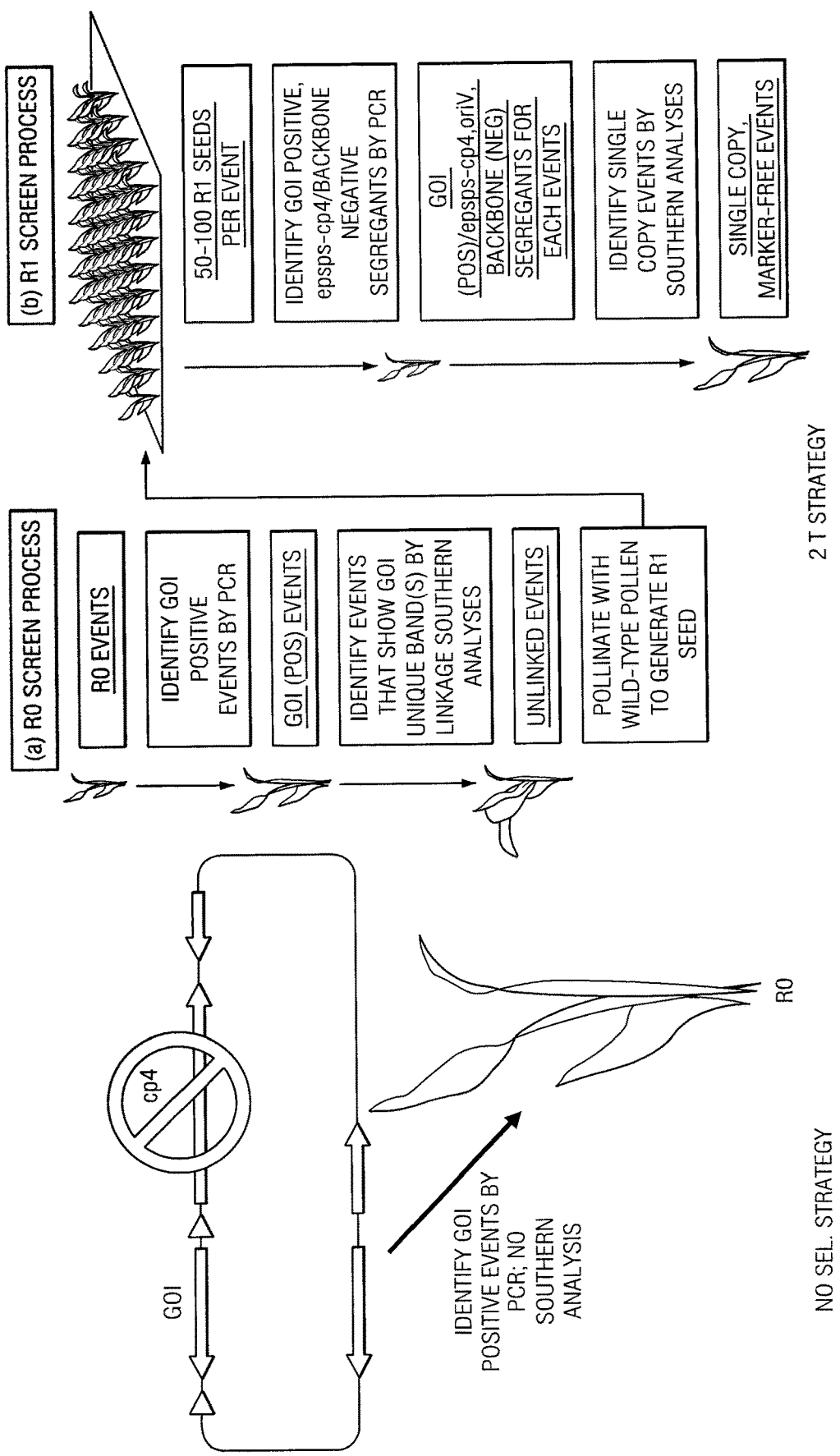
FIG. 1 Schematic comparison of no selection ("no sel") and 2T transformation protocols. (For further details on 2T strategy, please see Huang et al 2004)

Development of many modern genetically transformed plant products involves stacking of multiple transgenic traits together to provide multiple value-added traits to farmers. A major bottleneck in this process is the presence of selectable marker genes, which are carried along with a gene of interest (GOI) during transformation, as the process has typically relied on the use of a selectable marker gene to ensure transformation of plant cells. Although various methods are available for removing selectable marker genes following transformation, these methods are often time consuming and not highly efficient.

The present invention eliminates the aforementioned bottleneck through the development of an efficient transformation process without requiring the use of a selectable marker gene, as well as efficient plant handling and screening methods for advancing transgenic events produced without selection. In particular, the invention relates to methods for improving plant transformation efficiency and subsequent regeneration without using selection, leading to the production of marker-free transgenic events. This is a significant breakthrough in the production of transgenic crop plants, as marker-less transformation (as well as subsequent regeneration of plants in the absence of a selective agent) avoids the complexity associated with marker removal, avoids biasing the genetic structure of resultant transformation events due to a need for initial expression of a selectable marker gene, and also avoids potential difficulties during the progeny advancement process (e.g. due to segregation of transgenes corresponding to a GOI relative to those that encode a selectable marker). The process also eliminates the need for use of an additional expression cassette for the selectable or screenable marker gene, thereby reducing the size of the transformation vector and providing associated benefits such as reducing the chances of silencing due to repetitive cassette sequences, promoter interference and simplified construction of transformation vectors.

High-throughput production of selectable marker-free transgenic plants requires efficient production of transformants. It is preferable that transformation without selection, more specifically without selection prior to obtaining regenerated shoots or whole plantlets (comprising shoots and roots), be carried out in the absence of a selective agent. In certain embodiments, the nucleic acid sequences transformed into a target plant cell may comprise no selectable marker gene. In other embodiments, a selectable marker gene or visual marker gene may be present, but the transformed cells and regenerating tissues are nevertheless not subjected to a selective agent to which the selectable marker gene specifies tolerance, resistance, or other assayable phenotype.

Further, these transformants are preferably non-chimeric (i.e. uniform) with respect to the presence of a GOI, since the presence of chimeric plant tissues, that are non-uniform with respect to the presence of a GOI, complicates further analysis, production, and identification of progeny plants comprising the GOI. It has thus been found that transformation, including subsequent regeneration steps, without selection to routinely produce non-chimeric transgenic plants requires efficient production of large transgenic sectors and rapid production of shoot primordia.

Further, in the absence of selective pressure, large numbers of plants may be regenerated, many or most of which lack a GOI. Thus, efficient methods for regenerating, growing, and identifying plants potentially comprising a GOI are provided. In certain embodiments, regeneration of plants is performed in a semi-solid medium prior to transplanting of putative transformants into soil. In other embodiments, the media may be liquid. In yet other embodiments, a combination of semi-solid and liquid media may be employed during the regeneration process, to facilitate plant handling, and to save time, money, and expense, during screening and transfers to the different growth conditions utilized during the tissue culture process. In still yet other embodiments, only liquid media are used during the regeneration process. In particular embodiments, regeneration on liquid media may enhance the transformation frequency of the cells contacted by a gene of interest.

The presence of a selective agent throughout the tissue culture steps leading to a regenerated transformed plant may bias the characteristics of the selected tissue, essentially by requiring a certain level of expression of the selectable marker in order for tissue to survive the selective pressure.

This may result, for instance, in a bias toward obtaining transgenic events with multiple or complex insertions of a heterologous nucleic acid sequence. Thus, the invention provides a method for obtaining a population or series of putatively transformed plants without the plants having been subjected to such a selective pressure during phases of tissue culture such as callus proliferation, pre-regeneration, and regeneration, and which plants may display an advantageous expression profile of a GOI, and/or advantageous characteristics relating to the molecular structure and genetic segregation of the transgene insertion site(s) found in a given event. In particular, such an advantageous characteristic may include, for instance, that a significant proportion of transformation events displays an advantageous level of expression of a GOI, or that a significant proportion of transformation events displays low copy number (i.e. 1-2 copies) insertions. In particular embodiments, the low copy number transformation events lack oriV or other vector backbone sequences, if such sequences were present in the original transformation construct that initially contacted plant cells at the start of the transformation process.

Transformation and regeneration without such selection, in accordance with the methods of the present invention, is reproducible and efficient. In certain embodiments, the transformation frequency (TF), as expressed for instance on the basis of the number of stably transformed uniform (i.e. non-chimeric) plants obtained, per immature embryo or other explant comprising cells contacted by a heterologous nucleic acid construct, is at least 3%, and may range from about 3% to about 60% depending upon the embryo size and cultural conditions including type of regeneration regeneration methods. In particular embodiments, the TF may range from about 10% to about 15%. Alternatively, TF may be calculated in other ways, for instance based on the number of transformed plants obtained, per number of plants regenerated and grown from such immature embryos or other explants.

In certain embodiments, the crop plant being transformed without selection is selected from among monocot crop plants, including the Poaceae, such as corn, rice, sorghum, wheat, rye, millet, sugarcane, oat, triticale, turfgrass, and switchgrass plants. In a particular embodiment, the crop plant is a corn (maize) plant. In certain embodiments, the transformation target tissue, e.g. explant, contacted by a heterologous nucleic acid sequence comprises meristematic tissue, such as an embryo, or a shoot meristem. In certain embodiments the explant is an embryo. In particular embodiments, the embryo is an immature embryo. In still further embodiments, the immature embryo is an immature corn embryo, and is between about 1.9 and 3.5 mm in size, or between about 1.6-1.8 mm in size. In particular embodiments, the immature corn embryo is between about 1.9 and 2.5 mm, and preferably about 2.3 mm in size. In other embodiments, the immature corn embryo is about 2.5-3.2 mm in size, or about 2.8-4.0 mm in size. The immature embryo may also be selected as a transformation target based on its developmental stage, or the timing of its isolation, days after pollination (DAP), for instance about 9-14 days DAP, or about 10-12 DAP.

To initiate a transformation process in accordance with the present invention, it is first necessary to select genetic components to be inserted into the plant cells or tissues. Genetic components can include any nucleic acid that is introduced into a plant cell or tissue using the method according to the invention. Genetic components can include non-plant DNA, plant DNA or synthetic DNA.

In a preferred embodiment, the genetic components are incorporated into a DNA composition such as a recombinant, double-stranded plasmid or vector molecule comprising at least one or more of following types of genetic components: (a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of polyadenylated nucleotides to the 3' end of the RNA sequence.

The vector may contain a number of genetic components to facilitate transformation of the plant cell or tissue and regulate expression of the desired gene(s). In one preferred embodiment, the genetic components are oriented so as to express an mRNA, which in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA.

Methods for preparing plasmids or vectors containing the desired genetic components are well known in the art. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters would include but are not limited to the nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (e35S), the light-inducible promoter from the small subunit of ribulose bisphosphate carboxylase (ssRUBISCO, a very abundant plant polypeptide). All of these promoters have been used to create various types of DNA constructs that have been expressed in plants.

Promoter hybrids can also be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive as described, and temporally regulated, spatially regulated, and spatio-temporally regulated. Other promoters that are tissue-enhanced, tissue-specific, or developmentally regulated are also known in the art and envisioned to have utility in the practice of this invention.

Promoters may be obtained from a variety of sources such as plants and plant DNA viruses and include, but are not limited to, the CaMV35S and FMV35S promoters and promoters isolated from plant genes such as ssRUBISCO genes. As described below, it is preferred that the particular promoter selected should be capable of causing sufficient expression to result in the production of an effective amount of the gene product of interest.

The promoters used in the DNA constructs (for example, chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

An mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes (see, for example U.S. Pat. No. 5,362,865). Other genetic components that serve to enhance expression or affect transcription or translational of a gene are also envisioned as genetic components.

The 3' non-translated region of the chimeric constructs should contain a transcriptional terminator, or an element having equivalent function, and a polyadenylation signal that functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 0385 962).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In one embodiment, the T-DNA does not comprise a selectable, screenable, or scoreable marker gene. Alternatively, the DNA to be transferred may contain a selectable, screenable, or scoreable marker gene, although in certain embodiments of the invention plant tissues are only selected or screened for the presence of the marker after regeneration has occurred. These genetic components are also referred to herein as functional genetic components, as they produce a product that serves a function in the identification of a transformed plant, or a product of agronomic utility. The DNA that serves as a selection device functions in a regenerable plant tissue, in particular a regenerated tissue, to produce a compound that would confer upon the plant tissue resistance to an otherwise toxic compound. Genes of interest for use as a selectable, screenable, or scoreable marker would include but are not limited to uidA encoding GUS, gfp, encoding green fluorescent protein (GFP), anthocyanin biosynthesis related genes (C1, B-peru), luciferase (LUX), and genes specifying resistance to antibiotics like kanamycin (Dekeyser et al., 1989), and herbicides like glyphosate (Della-Cioppa et al., 1987). Other selection methods can also be implemented including but not limited to tolerance to phosphinothricin, bialaphos, and positive selection mechanisms and would still fall within the scope of the present invention.

The present invention can be used with any suitable plant transformation plasmid or vector containing a selectable or screenable marker and associated regulatory elements as described, along with one or more nucleic acids expressed in a manner sufficient to confer a particular trait. Examples of suitable structural genes of agronomic interest envisioned by the present invention would include but are not limited to genes for insect or pest tolerance, herbicide tolerance, genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms (see for example, Bird et al., 1991). The RNA could also be a catalytic RNA molecule (for example, a ribozyme) engineered to cleave a desired endogenous mRNA product (see for example, Gibson and Shillitoe, 1997). More particularly, for a description of anti-sense regulation of gene expression in plant cells see U.S. Pat. No. 5,107,065 and for a description of gene suppression in plants by transcription of a dsRNA see U.S. Pat. No. 6,506,559, U.S. Patent Application Publication No. 2002/0168707 A1, and U.S. patent application Ser. No. 09/423,143 (see WO 98/53083), Ser. No. 09/127,735 (see WO 99/53050) and Ser. No. 09/084,942 (see WO 99/61631), all of which are incorporated herein by reference. Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet that one desires, for example, to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

Technologies for the introduction of DNA into cells are well known to those of skill in the art and can be divided into categories including but not limited to: (1) chemical methods; (2) physical methods such as microinjection, electroporation, and micro-projectile bombardment; (3) viral vectors; (4) receptor-mediated mechanisms; and (5) *Rhizobia*-mediated (e.g. *Agrobacterium*-mediated) plant transformation methods (e.g. Broothaerts et al., 2005).

For *Agrobacterium*-mediated transformation, after the construction of the plant transformation vector or construct, said nucleic acid molecule, prepared as a DNA composition in vitro, is introduced into a suitable host such as *E. coli* and mated into another suitable host such as *Agrobacterium*, or directly transformed into competent *Agrobacterium*. These techniques are well-known to those of skill in the art and have been described for a number of plant systems including soybean, cotton, and wheat (see, for example U.S. Pat. Nos. 5,569,834 and 5,159,135, and WO 97/48814, herein incorporated by reference in their entirety).

The present invention encompasses the use of bacterial strains to introduce one or more genetic components into plants. Those of skill in the art would recognize the utility of *Agrobacterium*-mediated transformation methods in such a process. A number of wild-type and disarmed strains of *Agrobacterium tumefaciens* and *Agrobacterium rhizogenes* harboring Ti or Ri plasmids can be used for gene transfer into plants. Preferably, the *Agrobacterium* hosts contain disarmed Ti and Ri plasmids that do not contain the oncogenes that cause tumorigenesis or rhizogenesis, respectively, which are used as the vectors and contain the genes of interest that are subsequently introduced into plants. Preferred strains would include but are not limited to *Agrobacterium tumefaciens* derived from strain C58, a nopaline-type strain that is used to mediate the transfer of DNA into a plant cell, octopine-type strains such as LBA4404 or succinamopine-type strains, for example, EHA101 or EHA105. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector (Broothaerts et al, 2005). The use of these strains for plant transformation has been reported and the methods are familiar to those of skill in the art.

The explants can be from a single genotype or from a combination of genotypes. Any corn seed that can germinate is a viable starting material. In a preferred embodiment, superior explants from plant hybrids can be used as explants. For example, a fast-growing cell line with a high culture response (higher frequency of embryogenic callus formation, growth rate, plant regeneration frequency, etc.) can be generated using hybrid embryos containing several genotypes. In one embodiment, an $F_1$ hybrid or first generation offspring of cross-breeding can be used as a donor plant and crossed with another genotype. Those of skill in the art are aware that heterosis, also referred to herein as "hybrid vigor", occurs when two inbreds are crossed. The present invention thus encompasses the use of an explant resulting from a three-way cross, wherein at least one or more of the inbreds is highly regenerable and transformable, and the transformation and regeneration frequency of the three-way cross explant exceeds the frequencies of the inbreds individually. Other tissues are also envisioned to have utility in the practice of the present invention. Explants can include mature embryos, immature embryos, meristems, callus tissue, or any other tissue that is transformable and regenerable.

Any suitable plant culture medium can potentially be used during the transformation process. Examples of such media would include but are not limited to Murashige and Skoog (1962), N6 (Chu et al., 1975); Linsmaier and Skoog (1965); Uchimiya and Murashige (1962); Gamborg's media (1968), D medium (Duncan et al., 1985), McCown's Woody plant media (McCown and Lloyd, 1981), Nitsch and Nitsch (1969), and Schenk and Hildebrandt (1972) or derivations of these media supplemented accordingly, as well as the numerous media described below. Those of skill in the art are aware that media and media supplements such as nutrients and growth regulators for use in transformation and regeneration and other culture conditions such as light intensity during incubation, pH, and incubation temperatures can be optimized for the particular variety of interest.

Following regeneration of plantlets comprising shoots, or shoots and roots, a selective agent may be applied to the plantlets, or parts of plantlets, for instance if a selectable marker gene was being transformed into the initial target plant cells along with a GOI, or, alternatively, if the GOI itself encodes a selectable marker. Thus, after a plant has been produced by the methods of the present invention, a selective agent may be applied to it, in accordance with the present invention, in order to assist with assaying or otherwise identifying a transformed plant displaying useful characteristics.

The present invention also comprises methods for efficient handling of regenerated plants, which allows identification of transformed plants comprising the GOI. These methods simplify and streamline the process of regenerating and growing the population of putatively transformed plants, saving time, space, and expense required by the process, and making the process commercially feasible.

In one embodiment, plant target tissue, such as immature corn embryos (IEs), is co-cultivated with an *Agrobacterium* strain comprising a GOI, for instance for 1-3 days at 23° C. followed by culturing at 30° C. for an additional ~7-10 days on either the same co-culture medium or on a callus proliferation medium. Embryos may be observed in order to identify which embryos are "responding" i.e. producing embryogenic callus that may be regenerated to form a plantlet. Responding embryos with callus, typically scutellar callus, are then transferred from the co-culture to a first pre-regeneration medium, or a first regeneration medium, with appropriate culture conditions of temperature, light, and nutrients to allow further growth of callus, and differentiation and regeneration. The calli may be placed onto or into a semi-solid regeneration medium. Alternatively, they may be placed on a support, such as felt and/or filter paper in a culture plate, which is in contact with a liquid regeneration medium, such that the callus can grow and differentiate.

As needed, the inoculated embryos may be cultured, for instance in the dark for 1-2 weeks at 30° C., including transfer to fresh nutrient medium. After dark incubation, the cultures may be grown in regeneration media under alternating periods of light and darkness, for instance 1-3 weeks of growth under a 16/8 light/dark cycle at about 27° C. with light intensity of about 100 μE, or as appropriate based on the plant species or variety in question, and the knowledge of one of skill in the art of plant tissue culture. Typically, initiation of plant regeneration begins within 1-3 weeks of the start of co-cultivation, especially if a callus phase of growth is present. The method may also comprise a pre-regeneration step, which comprises use of a basal plant tissue culture medium supplemented with reduced levels of auxin(s) than is used in callus proliferation medium.

After about 2-3 weeks of culture and regeneration on semi-solid or liquid media, the regenerating plants from a single explant, for instance from immature embryos (IEs), may be transferred to a single growth medium container. One such example is a PHYTATRAY (Sigma-Aldrich, St. Louis, Mo.) comprising either semi-solid or a liquid plant tissue culture regeneration medium and grown for about 4 weeks before transferring the resulting plants to growth media for hardening off the plants, such as growth plugs in soil. Because transplantation to soil is a time and labor intensive process, it may be preferable to screen individual plants prior to their transplantation, or even prior to their being placed in a PHYTATRAY, for the presence of the GOI or other trait of interest. The number of regenerated plantlets in the absence of selective pressure may be 20-50× higher than would be found in a similar experiment, using a selective agent during callus growth and plant regeneration. Thus, a process for handling the large number of plants, for instance for transferring them from the tissue culture phase to growth under non-sterile conditions, is provided. Use of horticultural plugs or individual culture tubes or trays under non-sterile conditions to allow growth and analysis of plantlets is a further embodiment of the invention. These plantlets may further be grown without necessarily labeling all individual plants, by appropriate grouping of growing plants to allow easy correlation between a given plant and the its tissue which is being subjected to one or more assays or screens to identify transformed plants comprising the GOI.

In one embodiment, a PCR-based screen may be employed to eliminate non-transformed plants prior to their transfer to growth media, including liquid growth media, for instance in PHYTATRAYs. Thus, for example, if about 5000 immature corn embryos are used in transformation with a bacterial strain, about 25,000 plants may be produced, requiring about 5,000 PHYTATRAYs. If about a 10% transformation frequency was achieved, an initial screen of the regenerating plants at the PHYTATRAY growth stage would result in about 2500 putatively transformed plants, corresponding to 500 responding embryos or requiring about 500 PHYTATRAYs, that would be transplanted to growth plugs in soil. The screening method may include pooling of tissues from regenerating plants from individual Phytatrays or any other growth container such as plugs. The pools are designed such that, through analysis of multiple pools, single members of a population can be identified without the need for individual analysis of each member of the population. One pooling method is to group all plants derived from an explant, preferably an IE, in a PHYTATRAY or similar growth vessel and negative containers are discarded, thereby greatly reducing efforts associated with plant handling and assaying. The number of plants pooled together could be further increased, to the detection limit of a PCR assay.

The growth plugs may be handled or grouped to maximize the efficiency of further screening steps, and to obviate the requirement for individually labeling the regenerated plants. For instance, the plugs may be grouped and oriented to correspond to an assay formatted to use a microtiter plate, for instance a 96-well plate by growing the plants in 96 plug groups. This would allow rapid and accurate correlations to be made between the results of an assay and the plants from which assay tissue was isolated. In certain embodiments, the assays to determine the presence or absence of a GOI in a putatively transformed regenerated marker-free plant may be selected from the group consisting of a PCR-based assay, Southern hybridization, DNA sequencing, northern blotting, western blotting, an immunoassay, and an assay for an enzymatic activity encoded by the transgenic DNA segment which contacted the target tissue during co-cultivation with *Agrobacterium*. In a particular embodiment, the assay is a PCR-based assay. In certain embodiments, the PCR-based or other assay is performed on plant tissue isolated from regenerated plants growing in PHYTATRAYs or equivalent, prior to transplantation to a soil-based growth medium.

The present methods are more efficient than other typical methods for obtaining marker-free transgenic plants, for instance *Agrobacterium*-mediated approaches using one or more T-DNA(s) comprising a GOI, and a selectable or screenable marker (FIG. 1). Advantages provided by various embodiments of the invention include:

1. The transformation construct is smaller, simplifying the cloning procedure.
2. Elimination of the marker gene expression cassette frees up expression elements that would have been required for the marker cassette, reducing concerns about recombinational stability due to the presence of repeated elements. Elimination of repetitive regulatory elements from the marker cassette also minimizes the possibility of gene silencing.
3. The screening process for $R_0$ plants is simpler. In the previous processes, at least two elements must be screened for, the GOI and the selectable marker gene. In the present method, there is no need to screen for a marker. Additionally, plants positive for a GOI needed to be screened to determine whether the marker gene insert is linked to the GOI insert, and often linkage was found, which interferes with the ability to identify plants lacking the selectable marker in a subsequent generation. In contrast, linkage is not an issue in the present method.
4. Improved efficiencies in progeny generations is also found. For prior methods such as 2-T transformation methods, a large population of $F_1$ or $R_1$ plants must be screened to identify GOI positive, marker-free plants. For plants produced by the present method, no segregation of a marker gene is needed.
5. Allows for quicker selection of the best GOI-containing events without the presence of the selectable marker gene thereby facilitating efficient stacking of multiple GOI, e.g. when the selectable marker gene encodes an agronomic trait of interest.

The invention provides methods to efficiently produce marker-free transgenic plants, generally capable of growth in a soil-based medium, within 7-10 weeks after an initial target explant is contacted by an exogenous nucleic acid. The high-throughput methods of the present invention allow development of an efficient transformation system without selection. In particular, simplification of handling of regenerating tissues and regenerated plants allows for mechanization of many steps, and saves time, money, and ergonomic burden. The system may produce about 4-6 usable marker-free transformation events (i.e. single copy events and vector backbone-free events) per transformation experiment using about 100 embryos, thus expediting a transformed plant product pipeline.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Marker-Free Transformation

Transformation of regenerable immature corn embryos may be performed via a *Rhizobia*-mediated protocol, e.g. as generally described by Cai et al. (U.S. Patent Application Publication 20040244075). In particular, a modified *Agrobacterium*-mediated method was used. Immature embryos with a size range of 1.9-2.5 mm, for instance about 2.3 mm, were selected from corn ears and co-cultivated with an ABI *Agrobacterium* strain C58 to mediate the transfer of DNA into the plant cells containing the recombinant construct of interest, for instance pMON93040 containing both GUS and CP4 EPSPS under the expression control of an actin promoter, to allow for both visual analysis of transformed cells and sectors, and to allow for use of a Weathermax™ glyphosate spray as a surrogate for a later, post-regeneration screen followed by a confirmation test by a PCR-based screen for transformed plants. Larger embryos, e.g. about 2.5 mm or up to about 3.2 mm in size, may also be used, and may be preferable where few plants per embryo are produced by reducing callus proliferation before pre-regeneration, and regeneration phases of tissue culture. Composition of media used below are given in Table 1. Following inoculation with *Agrobacterium*, embryos were transferred to Lynx 1947 or Lynx 1898 for co-culture for a period of 1-3 days at 23° C., followed by additional 7-14 days at 30° C. on the same plate or on a callus proliferation medium (e.g., Lynx 1316), followed by growing on a pre-regeneration medium (Lynx 1844; 2232; 2197) or a regeneration medium (Lynx 1344, 2282, 2379 etc. Final growth of the plants can be achieved by two methods: 1) transferring plants from each embryo derived callus to a Phytatray™ containing Lynx 1607 or 2) transferring plants from each embryo derived callus to a Phytatray™ containing liquid Lynx 2168. Plants were allowed to grow in Phytatray™ for a period of about 4 wks before transferring them to plugs (Q Plugs by International Horticultural Technologies, Hollister, Calif.). One week prior to transferring the plants to plugs, samples from the plants are taken while the plants are still inside the Phytatray™ and assayed to remove plants without the GOI. Approximately, 10 days post-plugging samples from each plant were taken for DNA analysis and GOI positive plants were identified and retained for further growth and development.

TABLE 1

Media compositions used in various aspects of the present invention. Function of representative media is identified.

| Media Components/L (Suppliers) | 1898 co-culture | 1947 | 1316 callus proliferation | 2133 | 2232 | 2197 | 2282 |
|---|---|---|---|---|---|---|---|
| MS Basal Salts (Phytotech) | 4.33 g | 4.33 g | 4.33 g | 4.33 g | 4.33 g | 4.33 g | 4.33 g |
| MS Vitamins (100X) (Phytotech) | 10 mL | 10 mL | 10 mL | 10 mL | 10 mL | 10 mL | 10 mL |
| MSFromm vitamins (1000X)* | 0 | 0 | 0 | 0 | 0 | 0 | 0 |
| Thiamine HCL (Sigma) | 0.5 mg | 0.5 mg | 0.5 mg | 0.5 mg | 0.5 mg | 0.5 mg | 0.5 mg |
| 2,4-D (Phytotech) | 0.5 mg | 0.5 mg | 0.5 mg | 0.5 mg | 0.2 mg | 0.2 mg | 0 |
| Sucrose (Phytotech) | 30 g | 30 g | 30 g | 30 g | 50 g | 50 g | 50 g |
| Proline (Sigma) | 1.38 g | 1.38 g | 1.38 g | 1.38 g | 1.38 g | 0 | 0 |
| Casamino Acids (Difco) | 0.5 g | 0.5 g | 0.5 g | 0.5 g | 0.5 g | 0.5 g | 0.5 g |
| pH | 5.8 | 5.8 | 5.8 | 5.8 | 5.8 | 5.8 | 5.8 |
| Low EEO Agarose (Sigma) | 5.5 g | 5.5 g | 0 | 5.5 g | 5.5 g | 0 | 0 |
| Phytagel (Sigma) | 0 | 0 | 3.0 g | 0 | 0 | 0 | 0 |
| Phytagar (Gibco) | 0 | 0 | 0 | 0 | 0 | 0 | 0 |
| Post autoclave additives | | | | | | | |
| Carbenicillin (Phytotech) | 50 mg | 50 mg | 500 mg | 500 mg | 50 mg | 500 mg | 500 mg |
| Acetosyringone (Aldrich) | 200 uM | 200 uM | 0 | 200 uM | 200 uM | 0 | 0 |

TABLE 1-continued

Media compositions used in various aspects of the present invention. Function of representative media is identified.

| | | | | | | |
|---|---|---|---|---|---|---|
| BAP (Sigma) | 0 | 0.01 mg | 0.01 mg | 0.01 mg | 0.01 mg | 0.01 mg | 0.01 mg |
| Glyphosate (Gateway Chemical) | 0 | 0 | 0 | 0 | 0 | 0 | 0 |
| Silver Nitrate (Sigma) | 3.4 mg | 3.4 mg | 3.4 mg | 3.4 mg | 3.4 mg | 3.4 mg | 3.4 mg |
| Abscisic acid | 0 | 0 | 0 | 0 | 0 | 0 | 0 |

| Media Components/L (Suppliers) | 2379 | 1844 pre-regeneration | 1344 regeneration | 2168 | 1607 growth | 1471 |
|---|---|---|---|---|---|---|
| MS Basal Salts (Phytotech) | 4.33 g | 4.33 g | 4.33 g | 4.33 g | 4.33 g | 4.33 g |
| MS Vitamins (100X) (Phytotech) | 10 mL | 10 mL | 10 mL | 10 mL | 10 mL | 10 mL |
| MSFromm vitamins (1000X)* | 0 | 0 | 1 mL | 0 | 0 | 0 |
| Thiamine HCL (Sigma) | 0 | 0 | 0 | 0 | 0 | 0 |
| 2,4-D (Phytotech) | 0 | 0.2 mg | 0 | 0 | 0 | 0 |
| Sucrose (Phytotech) | 60 g | 40 g | 30 g | 60 g | 60 g | 60 g |
| Proline (Sigma) | 0 | 0 | 1.38 g | 0 | 0 | 0 |
| Casamino Acids (Difco) | 0 | 0 | 0.5 g | 0 | 0 | 0 |
| pH | 5.8 | 5.8 | 5.8 | 5.8 | 5.8 | 5.8 |
| Low EEO Agarose (Sigma) | 0 | 0 | 0 | 0 | 0 | 0 |
| Phytagel (Sigma) | 0 | 0 | 3.0 g | 0 | 0 | 0 |
| Phytagar (Gibco) | 0 | 6 | 0 | 0 | 6 | 6 |
| Post autoclave additives | | | | | | |
| Carbenicillin (Phytotech) | 500 mg | 500 mg | 250 mg | 500 mg | 100 mg | 100 mg |
| Acetosyringone (Aldrich) | 0 | 0 | 0 | 0 | 0 | 0 |
| BAP (Sigma) | 0.01 mg | 0 | 3.5 mg | 0 | 0 | 0.02 mM |
| Glyphosate (Gateway Chemical) | 0 | 0 | 0 | 0 | 0 | 0 |
| Silver Nitrate (Sigma) | 0 | 0 | 0 | 0 | 0 | 0 |
| Abscisic acid | 0 | 0.26 mg | 0 | 0 | 0 | 0 |

*1000X stock contains Nicotinic acid –1.25 g; Pyridoxine HCL 0.25 g; Thiamine HCl 0.25 g; Calcium Pantothenate 0.25 g Example 2

Efficient Development of of Transgenic Sectors without Selection Pressure During Callus Proliferation A system for efficient regeneration of transgenic plants in the absence of a selection agent was developed. Following co-culture of an explant with *Agrobacterium* (4 days on Lynx 1898 medium (Table 1), callus proliferation commenced on Lynx 1316 (Table 1), for 10-14 days, without selection. Next, pre-regeneration of callus tissue was performed for 10 days on Lynx 1844 medium (Table 1), followed by regeneration on Lynx 1344 (Table 1) for 10 days, and Lynx 1471 for 3 weeks (Table 1). All steps except for culture on Lynx 1471 were performed without use of a selective agent; thus callus growth and plant regeneration occurred without a selective agent for about 4 weeks after co-cultivation. Growth of regenerating plants in the last step, on Lynx 1471, was performed in the presence of a low level of glyphosate (0.02 mM, v/v) to estimate the maximum possible transformation frequency. Prior to transferring tissues to Lynx 1471 media, 24 independent embryo-derived calli and associated tissues were stained for GUS activity at 4 weeks post-transformation. Four GUS positive shoots were identified, thus demonstrating ~16% transformation efficiency.

Figure 2:
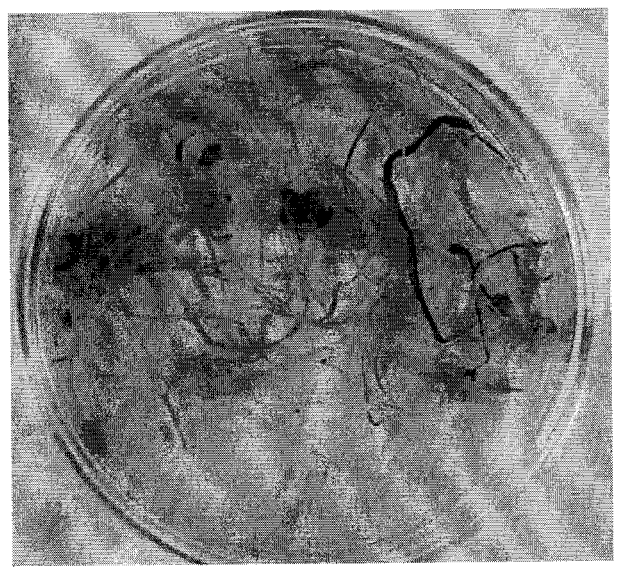
FIG. 2 Histochemical analysis using GUS of representative regenerating lines.

Further plant growth was achieved by transferring tissues to Lynx 1471 in Phytatrays, and a total of 43 transgenic events were regenerated, all of which survived upon transfer to soil. The transformation and copy number analysis is shown in Table 2. About 14% of the total plants that survived were escapes, but about 45% of the plants were transformed with 1-2 inserts. Histochemical analysis of representative regenerating callus lines, 5 weeks post-transformation is shown in FIG. 2.

TABLE 2

Efficient transformation using selection only during last step of plant regeneration indicates efficient transformed sector formation without selection.

| Expt | # Explants | # to soil (survived) | 0-copy | 1-copy | 2-copy | >2copy | 1 copy and oriV minus | 2 copy and oriV minus |
|---|---|---|---|---|---|---|---|---|
| 6678 | 200 | 43 (21.5%) | 6 (14%) | 12 (28%) | 7 (16%) | 8 (19%) | 9 (21%) | 4 (9%) |

Example 3

Additional Corn Transformation and Regeneration Experiments, and Screening of Putative Transformed Plants Three more studies were performed to confirm that efficient regeneration of transgenic sectors was routinely possible without applying selection at any stage. The plasmid used was pMON93040, described above. Following co-culture on Lynx 1898 for 1 day, callus proliferation was performed on Lynx 1316 for 10 days, pre-regeneration on Lynx 1844 for 10 days, and regeneration on Lynx 1344 for 3 days, followed by growth on Lynx 1607. A single corn ear was used to isolate the embryos for each experiment, and the embryos ranged in size from 2.8-3.2 mm. In two of the studies, embryo inoculation was performed directly isolating embryos into *Agrobacterium* suspension at $O.D._{.660}=1.0$, while in the other study embryos were first isolated into 1 ml of liquid Lynx 1013 medium (1 Liter: MS Basal Salts (Phytotech): 2.165 g; MS Vitamins (100×; Phytotech): 10 ml; Sucrose (Phytotech): 68.5 g; Proline (Fisher): 0.115 g.; Glucose (Phytotech) 36 g. The medium was adjusted to pH 5.4 with KOH, and filter sterilized), followed by inoculation using an *Agrobacterium* suspension at $O.D._{.660}=1.0$. Results of the studies are listed in Table 3.

TABLE 3

Additional Corn Transformation without Selection.

| Expt | # IES | # plants in plugs | # gus/CP4 positive plants | #Events/100 plants (estimated) |
|---|---|---|---|---|
| 6688-2 | 110 (48)* | 230 | 8 | 3.5 |
| 6698-2 | 110 (52)* | 240 | 9 | 3.8 |
| 6700-2 | 100 (50)* | 253 | 20 | 7.9 |
| | | | Average/100 plants | 5.1 |

Figure 3:
FIG. 3 Recovery of glyphosate-tolerant events through "no selection" approach after spraying the plants with glyphosate solution.

*data in parenthesis indicates # of responding embryos; ~50% embryos responded to culture
"# IES" = number of inoculated immature embryos At the end of the regeneration cycle, plants from each experiment were transplanted into plugs and over 95% plants survived the transfer, demonstrating that propagation plugs offer an improved way to handle large number of plants. About ten days post transplanting, leaf punches from individual plants were assayed for GUS activity using histochemical staining, and GUS positive plants were transplanted for further growth and histochemical analysis. To further demonstrate the transformation frequency and to improve the overall efficiency of the protocol, a surrogate for a PCR-based screen was developed, whereby 1% Weather-Max™ (Glyphosate) was applied to GUS negative plants. An additional five glyphosate tolerant plants were identified (3 from experiment 6700-2, 1 from 6698-2 and 1 from experiment 6688-2 (see FIG. 3 for representative plants). A total of 37 plants were obtained from 723 plants in plugs, yielding an estimated 5% success rate on a per plant basis (Table 3). The results of transformation without selection, using immature embryos demonstrate that the process is efficient, with an average 5% transformation frequency based on the number of plants screened.

To further demonstrate reproducibility of the transformation protocol without selection and to improve the overall efficiency of the protocol, a surrogate for a PCR-based screen was developed, whereby 1% WeatherMax™ (Glyphosate) was applied after the end of the regeneration phase which was carried out without selection. in PHYTATRAYs. Results are shown in Table 4 and Table 5.

TABLE 4

Efficient and Reproducible Corn Transformation without Selection

| Expt | # embryos inoculated | IE size | # phytas screened | Estimated # plants | #cp4+ events | #Events/100 plants (estimated) |
|---|---|---|---|---|---|---|
| 6705-1 | 130 | 2.8-3.2 | 19 | 380 | 9 | 2.4 |
| 6705-2 | 140 | 2.8-3.2 | 13 | 260 | 7 | 2.7 |
| 6706-3 | 110 | 1.8-2.0 | 22 | 440 | 35 | 8 |
| 6829-1 | 100 | 2.8-3.0 | 28 | 560 | 27 | 4.8 |
| 6829-2 | 100 | 2.8-3.0 | 30 | 600 | 43 | 7.2 |
| 6829-3 | 80 | 2.8-3.2 | 10 | 200 | 11 | 5.5 |
| 6829-4 | 80 | 2.8-3.2 | 9 | 180 | 3 | 1.7 |
| 6829-5 | 80 | 2.8-3.2 | 8 | 160 | 4 | 2.5 |
| 6829-6 | 80 | 2.8-3.2 | 7 | 140 | 2 | 1.4 |
| | 900 | | 146 | 2920 | 141 | 4.8 |

TABLE 5

Efficient Recovery of Events with Lower Copy Inserts from Transformation without Selection.

| Expt | # embryos inoculated | # Events survived in plugs | Total (1-2 copy) |
|---|---|---|---|
| 6705-1 | 130 | 9 | 7 (77.7%) |
| 6705-2 | 140 | 7 | 2 (28.6%) |
| 6706-3 | 110 | 35 | 29 (82.9%) |
| 6829-1 | 100 | 27 | 18 (66.7%) |
| 6829-2 | 100 | 43 | 30 (69.8%) |
| 6829-3 | 80 | 11 | 8 (72.2%) |
| 6829-4 | 80 | 3 | 2 (66.7%) |
| 6829-5 | 80 | 4 | 3 (75.0%) |
| 6829-6 | 80 | 2 | 1 (50.0%) |
| Total | 900 | 141 | 100 (70.9%) |

The results indicate that out of a total of 900 embryos, 141 glyphosate tolerant plants were produced, including 100 with lower copy number (1-2 copies) of the gene of interest, i.e. an average of about 15% TF based on the number of immature embryos inoculated.

Further screening (Table 6) showed that, of the 90 events screened by Southern analysis out of the 100 low copy number events shown in Table 5, 79 independent integration events were present. Sister events are events with same band pattern and coming from the same explants. Higher transformation frequency lead to higher percentage of transgenic events with sister events. Nevertheless, the frequency was very low and Southern analysis revealed ~5% exhibiting clonality, especially when TF is >30% (Tables 5 and 6).

TABLE 6

Efficiency of Transformation without Selection- Number of Independent Integration Events Produced.

| Expt | # Events analyzed by Southern blot (1 & 2 copy) | # Events with sister |
|---|---|---|
| 6705-1 | 1 | 0 |
| 6705-2 | 7 | 0 |
| 6706-3 | 25 | 3 |
| 6829-1 | 16 | 1 |
| 6829-2 | 27 | 1 |
| 6829-3 | 8 | 0 |
| 6829-4 | 2 | 0 |
| 6829-5 | 3 | 0 |
| 6829-6 | 1 | 0 |
| Total | 90 | 5 |

Example 4

Figure 4:
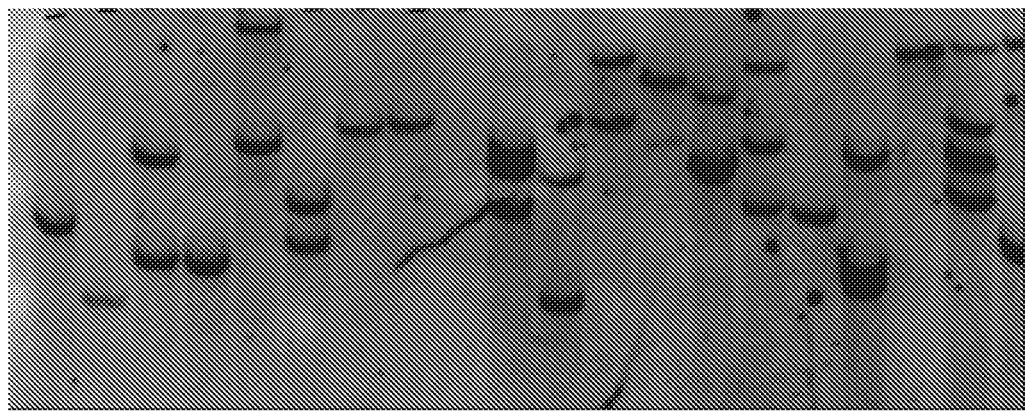
FIG. 4 Representative Southern analysis data from selected $R_0$ plants as described in Example 4.
Figure 5:
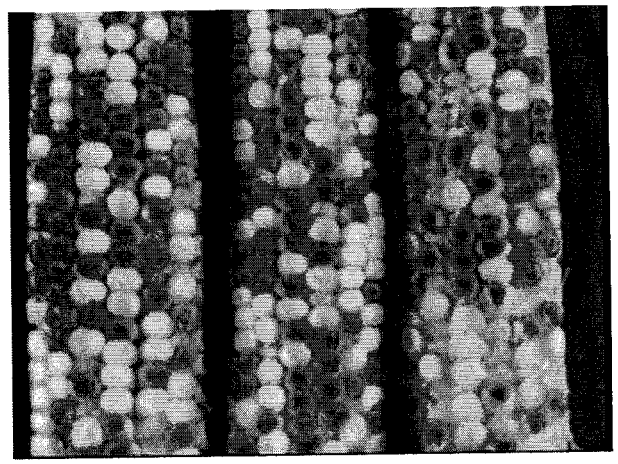
FIG. 5 Germline transmission and segregation of GUS gene to next generation was validated using $R_0$ pollen and backcrossing with parental line.
Figure 6:
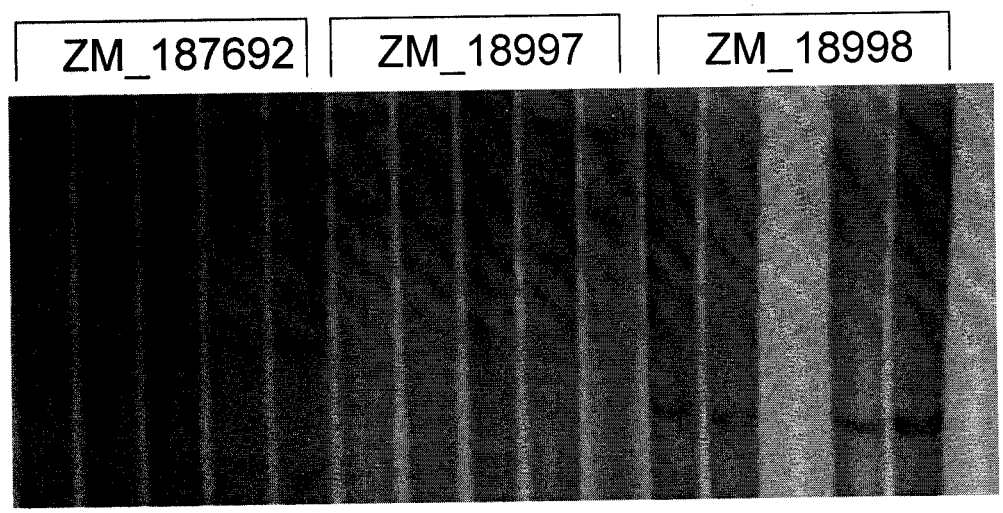
FIG. 6 Southern analysis data from progeny of selected independent transformation events, demonstrating stable transmission of transformed sequences (CP4 gene).

Confirmation of Chromosome Integration of a Transferred DNA Following Transformation and Regeneration without Selective Pressure Genomic DNA was isolated from leaves of $R_0$ plants, e.g. using procedures described by Dellaporta (1983). Genomic DNA (20-30 µg) was digested with HindIII, separated on a 0.7% (w/v) agarose gel, and transferred to positively charged nylon membranes (Roche Molecular Biochemicals, Indianapolis, Ind.). Pre-hybridization, hybridization, washing and detection of the membranes were conducted using a non-radioactive DIG-based system (Roche Molecular Biochemicals) following the manufacturer's protocols. DNA sequence from the CP4 gene was labeled by PCR to produce probes. The HindIII enzyme cuts once with in the vector (near the 5' end of the CP4 expression cassette, therefore, the number of bands by Southern blot corresponds to the number of CP4 gene copies. Southern analysis was performed on selected plants described in Table 3 (i.e. 22 lower copy events were selected). Representative Southern analysis data of $R_0$ plants is shown in FIG. 4. Analysis revealed that eight (single copy, oriV negative) events were produced from the population of 37 events produced from 320 embryos (Table 3). To further confirm germline transmission to the next generation, $R_0$ plants were crossed with the parental non-transformed inbred corn line. In this study, $R_1$ plants from three independent lines were used; ZM_187694 (4 copies—cp4); ZM_189983 (0 copy, cp-4—a possible cp4 truncated event); ZM_187738 (3 copies—cp4). Histochemical analysis of gus expression of the developing ears indicated that positive kernels to non-expressing kernels in 1:1 ratio, indicating germline transmission of the transgene and linkage (FIG. 5). This result confirms germline transmission of a transgene using transgenic events produced without selection. Progeny from three additional independent events ZM_187692, ZM_18997, and ZM_18998 were also analyzed by Southern blot analysis using CP4 gene as a probe (FIG. 6), showing that all progenies derived from three different $R_0$ plants showed the expected pattern, i.e. stable transmission of the transgenic event to the next generation.

Example 5

Efficient Plant Handling

A method for efficient handling of multiple plants is an important component of an efficient plant transformation system that does not use a selective agent prior to obtaining a regenerated plant. This is because a large number of plants may need to be screened in order to identify transformed plants with appropriate copy number and complexity of insertions, as well as expression of the GOI. This "handling" (e.g. transfer or transplantation to media or soil for further growth; and maintenance of identity during screening steps) allows multiple plantlets to be processed inside a container holding the individual plugs or culture tubes, while maintaining the plants' individual indentity, and also facilitates data capture without labelling of individual plants. The combination of growing plants in "horticultural plugs," skipping labelling of individual plants, and developing a protocol to capture assay data for identifying and moving forward the desired events, expedites the transformation pipeline based on non-selection during gene transfer and regeneration. In summary the present invention relates to the development of an efficient plant transformation system without selection, plant handling and data capture.

Figure 7:
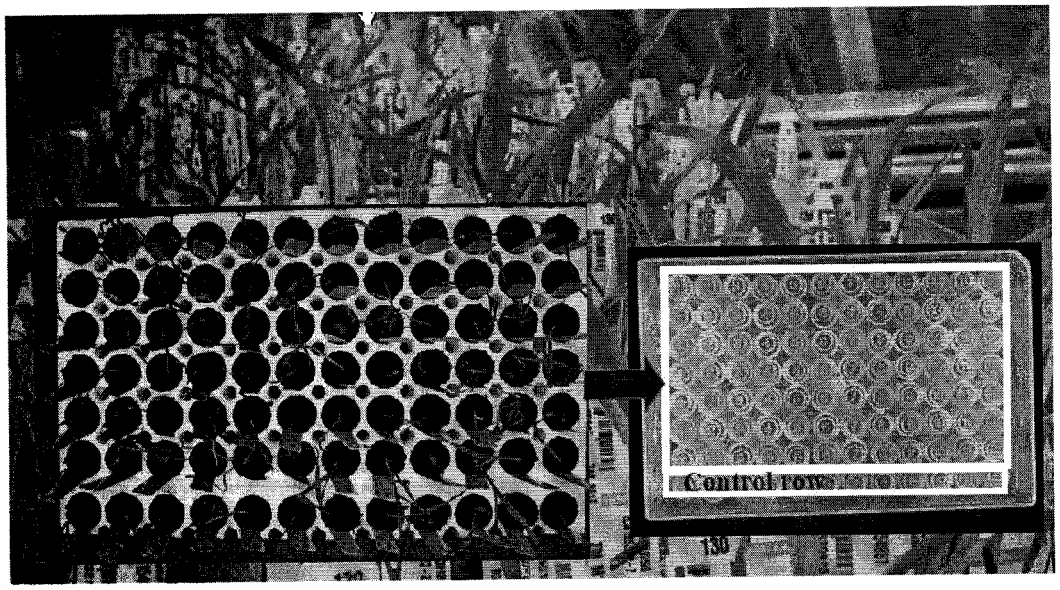
FIG. 7 Arrangement of growth plugs to allow easy identification of individual plants following assay for presence of transgenic sequence.

Putatively transformed plants, regenerated from calli that have been co-cultivated with an *Agrobacterium* strain comprising a gene of interest, can be transplanted, e.g. from a Phytatray™ into soil in growth plugs. Use of these plugs can streamline sampling and analysis of the plants, and save growth space. For instance, the plugs are arranged in a pattern that corresponds to the wells of, for instance, a 96 well microtiter plate (e.g. FIG. 7), if assays of samples from the plants are to be performed in such microtiter plates. This allows facile identification of plants displaying an assay phenotype of interest without the need to label individual plants.

Early elimination of plants not comprising the GOI is accomplished by a PCR-based or other molecular screen while plants are being regenerated in PHYTATRAYs on semi-solid or liquid media, and prior to transplantation of plants to growth plugs or soil.

Example 6

Semi-Solid Media for Culture During Regeneration of Transformed Plants

Figure 8:
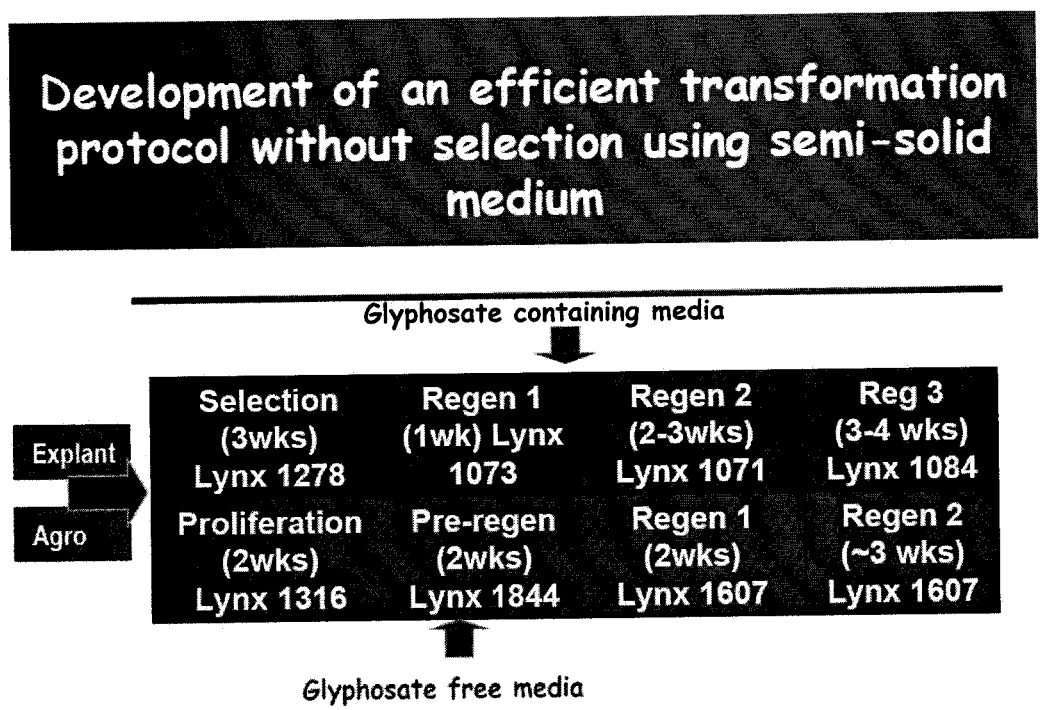
FIG. 8 Schematic diagram of regeneration protocols utilizing semi-solid media-comparing selection and no selection approaches.

Semi-solid media for culture during the callus growth, pre-regeneration, and regeneration phases of the transformation and tissue culture process allows efficient tissue manipulation. FIG. 8 summarizes a transformation study carried out without a selective agent (lower panel), as compared to a parallel study wherein plant tissue was grown in the presence of a selective agent (top panel). See Tables 1 and 7 for media components. Callus proliferation, pre-regeneration, and regeneration phases were carried out in semi-solid media as shown. After the second regeneration phase, plants are transplanted into growth plugs and assayed for the presence of a GOI.

TABLE 7

Media compositions used in a previous method comprising semi-solid glyphosate containing selection media (Cai et al.; U.S. Patent Applic. Publn. 2004/00244075).

| Media Components/L (Suppliers) | 1233 (co-culture) | 1278 (selection) | 1073 ($1^{st}$ regeneration) | 1071 ($2^{nd}$ regeneration) | 1084 (rooting) |
|---|---|---|---|---|---|
| MS Basal Salts (Phytotech) | 2.165 g | 4.33 g | 4.33 g | 4.33 g | 2.165 g |
| MS Vitamins (100X) (Phytotech) | 10 mL | 10 mL | 0 | 0 | 0 |
| MS Fromm Vitamins (1000X)* | 0 | 0 | 1 mL | 1 mL | 0 |
| BAP (Sigma) | 0 | 0.01 mg | 3.5 mg | 0 | 0 |
| Thiamine HCL (Sigma) | 0.5 mg | 0.5 mg | 0 | 0 | 0 |
| 2,4-D (Phytotech) | 3 mg | 0.5 mg | 0 | 0 | 0 |
| NAA (Sigma) | 0 | 0 | 0 | 0 | 0.5 mg |
| IBA (Sigma) | 0 | 0 | 0 | 0 | 0.75 mg |
| Sucrose (Phytotech) | 20 g | 30 g | 30 g | 0 | 20 g |
| Glucose (Phytotech) | 10 g | 0 | 0 | 10 g | 0 |
| Maltose (Phytotech) | 0 | 0 | 0 | 20 g | 0 |
| Proline (Sigma) | 115 mg | 1.38 g | 1.38 g | 0 | 0 |
| Casamino Acids (Difco) | 0 | 0.5 g | 0.05 g | 0.5 | 0 |
| Asparagine monohydrate (Sigma) | 0 | 0 | 0 | 0.15 | 0 |
| Myo-inositol (Sigma) | 0 | 0 | 0 | 0.1 g | 0 |
| Low EEO Agarose (Sigma) | 5.5 g | 0 | 0 | 0 | 0 |
| Phytagel (Sigma) | 0 | 3 g | 3 g | 3 g | 3 g |
| Acetosyringone (Aldrich) | 200 uM | 0 | 0 | 0 | 0 |
| Carbenicillin (Phytotech) | 500 mg | 500 mg | 250 mg | 250 mg | 0 |
| Glyphosate (Gateway Chemical) | 0 | 0.1 mM | 0.1 mM | 0.1 mM | 0.1 mM |
| Silver Nitrate (Sigma) | 3.4 mg | 3.4 mg | 0 | 0 | 0 |
| pH | 5.2 | 5.8 | 5.8 | 5.8 | 5.8 |

*Comprising 1250 mg/L nicotinic acid (Sigma), 250 mg/L pyridoxine HCl (Sigma), 250 mg/L thiamine HCl (Sigma), and 250 mg/L calcium pantothenate (Sigma).

Example 7

Liquid Culture During Regeneration of Transformed Plants

Figure 9A:
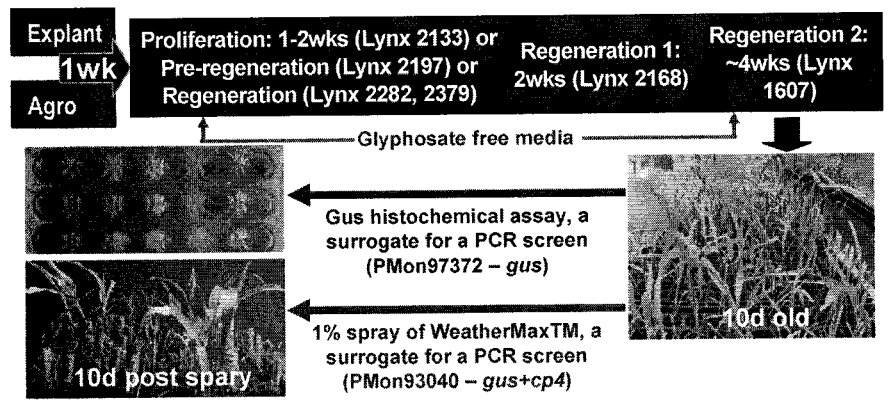
FIG. 9A and FIG. 9B Regeneration protocols using liquid culture without selection prior to obtaining a regenerated plant-comparison of proliferation media.
Figure 9B:
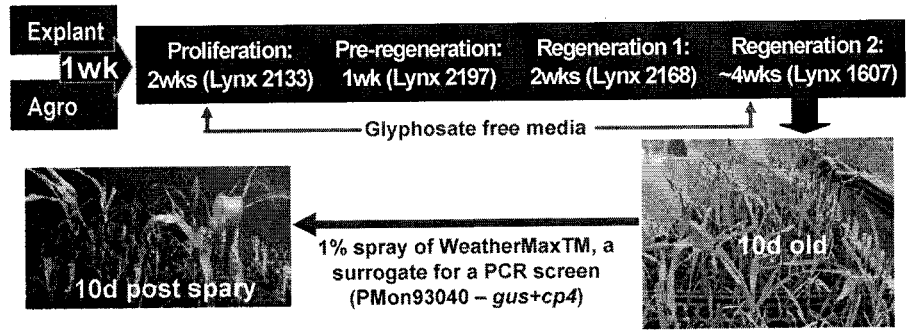

Liquid culture during the callus growth, pre-regeneration, and regeneration phases of the transformation and tissue culture process enables efficient tissue manipulation. FIG. 9 illustrates transformation and regeneration studies carried out without a selective agent prior to regeneration. Callus proliferation, pre-regeneration, and regeneration phases were carried out in liquid, glyphosate-free media as shown. After the second regeneration phase, which may alternatively occur in a semisolid medium, plants were transplanted into growth plugs. GUS histochemical assays may be combined with PCR-based or other screens, such as a surrogate screen with, for instance, glyphosate, to detect expression of, for instance, glyphosate tolerance in the regenerated plant tissue. These experiments were performed either using a vector without a marker gene (i.e. pMON97372) or with a marker gene (pMON93040).

The plasmid for the study illustrated in FIG. 9 was pMON93040 containing cp4 and gus genes. Embryos from each ear were isolated into Petri dishes with 1 ml of liquid Lynx 1013 medium and co-cultured on Lynx 1947. Embryos were divided among various treatments as shown in the Table 8 below, including 8 weeks with selection (Treatment 1); 8 weeks without selection, liquid culture, with growth in solid medium in PHYTATRAY (Treatment 2); and 8 weeks without selection, liquid culture, with growth in liquid medium in PHYTATRAY (Treatment 3). Transformation using no selection was quite efficient (~⅓x) compared to what was achieved using selection. A summary of the results of the "liquid-plug" method are shown in Table 8. When a small sample of explants was carried forward using only liquid culture (i.e. treatment #3, using Lynx 2168 as the final growth medium), the efficiency was higher and nearly as high as what was obtained with selection. Liquid culture appears to promote more efficient regeneration of transgenic events as evident from Table 9. It is likely that elimination of sub-culture reduces stress and hastens plant regeneration.

TABLE 8

Efficient transformation using "liquid-plug scheme" and without using selection.

| Exp# | Treatment | IE Size | # Explants (IEs) | # IE with events | % TF |
|---|---|---|---|---|---|
| 7530-1 | Liquid Selection - 8 wks | 2.5-2.8 | 30 | 14 | 46.7 |
| 7531-1 | | 1.9-2.1 | 30 | 16 | 53.3 |
| 7532-1 | | 1.9-2.2 | 30 | 4 | 13.3 |
| 7533-1 | | 2.5-2.8 | 30 | 7 | 23.3 |
| | Total | | 120 | 41 | 34.2 |
| 7529-1 | Transformation without selection using liquid culture with a PHYTATRAY step + glyphosate spray screening | 2 | 60 | 5 | 8.3 |
| 7530-2 | | 2.5-2.8 | 88 | 16 | 18.2 |
| 7531-2 | | 1.9-2.1 | 68 | 13 | 19.1 |
| 7532-2 | | 1.9-2.2 | 127 | 11 | 8.7 |
| | Total | | 343 | 45 | 13.1 |
| 7530-3 | Transformation without selection using | 2.5-2.8 | 21 | 9 | 42.9 |
| 7531-3 | | 1.9-2.1 | 18 | 10 | 55.6 |

TABLE 8-continued

Efficient transformation using "liquid-plug scheme" and without using selection.

| Exp# | Treatment | IE Size | # Explants (IEs) | # IE with events | % TF |
|---|---|---|---|---|---|
| 7532-3 | liquid culture with glyphosate spray screening after transplanting in plugs | 1.9-2.2 | 22 | 4 | 18.2 |
| | Total | | 61 | 23 | 37.7 |

TABLE 9

Efficiency of transformation as related to regeneration efficiency.

| Exp# | Treatment | # Explants (IEs) | # IE with events | % TF | # Plants in plugs | # Events/ 100 plants |
|---|---|---|---|---|---|---|
| 7530-3 | Transformation | 21 | 9 | 42.9 | 208 | 4.3 |
| 7531-3 | without selection | 18 | 10 | 55.6 | 208 | 4.8 |
| 7532-3 | using liquid culture with glyphosate spray screening after transplanting in plugs | 22 | 4 | 18.2 | 208 | 1.9 |
| | Total | 61 | 23 | 37.7 | 624 | 3.7 |

Example 8

Transformation Efficiency as Related to Duration of Callus Proliferation Phase

The role of the duration of the callus proliferation phase on transformation frequency is illustrated in Table 10. Reducing the length of the callus phase improved TF, producing plants faster.

TABLE 10

Longer callus proliferation phase negatively impacts transformation without selection.

| Exp# | Treatment | IE Size | # To sel | # IE with events | % TF |
|---|---|---|---|---|---|
| 7533-1 | Sel - 8 wks liquid culture. | 2.5-2.8 | 30 | 7 | 23.3 |
| 7533-2 | No selection - 8 wks (2 wks on Lynx 2133) | 2.5-2.8 | 104 | 8 | 7.7 |
| 7533-3 | No selection - 8 wks (1 wk on Lynx 2133) | 2.5-2.8 | 97 | 19 | 19.6 |

Example 9

Transformation and Regeneration Using Rapid Liquid Culture without Selection

To further streamline the process, a rapid liquid cycle (RLC) protocol was developed, 6 weeks in length, wherein the callus proliferation step (Lynx 2133) was omitted. The steps in the transformation scheme included: pre-regeneration (Lynx 2197), and regeneration phases (Lynx 2168 and Lynx 1607 e.g. FIG. 9 and Table 11). pMON93040, containing Cp4 and gus genes, was used for this study. Embryos from each ear were isolated onto a Petri dish with liquid medium (Lynx 1013), co-cultured on Lynx 1947 medium, and divided among the treatments shown in Table 11. Treatments included comparing TF of embryos with or without selection, and comparing the effect of either 1 or 2 weeks on Lynx 2197 proliferation medium. As shown in Table 11, a reduction of duration on Lynx 2197 proliferation medium did affect TF. However, transformation without selection resulted in TF comparable to the TF achieved using selection when an optimum duration of growth on pre-regeneration medium was used.

TABLE 11

Efficient Transformation Using Rapid Liquid Culture Protocol, without Selection.

| Exp# | Treatment | # Explants (IEs) | # IE with events | % TF | # plants to plugs | Events/ 100 plants |
|---|---|---|---|---|---|---|
| 7962-3 | Sel - 6 wks liq. | 65 | 37 | 56.9 | N/A | N/A |
| 7963-1 | | 65 | 16 | 24.6 | | |
| | Total 8 wks liq sel | 130 | 53 | 40.8 | | |
| 7965-1 | 6 wks No | 60 | 27 | 45.0 | 548 | 4.9 |
| 7963-2 | selection with 2 wks on Lynx 2197 | 60 | 18 | 30.0 | 342 | 7 |
| | Total No Sel. 2 wks Lynx 2197 | 120 | 45 | 37.5 | 890 | 5.1 |
| 7965-1 | 6 wks No | 60 | 12 | 20 | 493 | 2.4 |
| 7963-2 | selection with 1 wk on Lynx 2197 | 60 | 13 | 21.7 | 274 | 4.7 |
| | Total No Sel. 1 wk Lynx 2197 | 120 | 25 | 20.8 | 767 | 3.2 |

In these experiments, the duration of the callus proliferation, pre-regeneration, and regeneration phases were further reduced, and use of selection was compared to growth on non-selective media. The reduction in required tissue handling steps further renders this method amenable to automation (See also Table 15).

A comparison of the expression level of selected plants obtained as described above revealed comparable levels of expression (Table 12) following PCR-based assay for the pinII 3' transcription termination signal.

TABLE 12

Expression analysis of plants categorized by copy number of transgene.

| Treatment | Copy # for PinII 3' UTR | # Plants assayed | Average Expression value for PinII 3' UTR | SD |
|---|---|---|---|---|
| RLC with selection | 1 | 70 | 1.432 | 1.5 |
|  | 2 | 28 | 1.902 | 2.6 |
| RLC with no selection* | 1 | 44 | 0.957 | 3.37 |
|  | 2 | 35 | 0.809 | 1.3 |

*Plants from "no selection" were 2 weeks older at the time of sampling

A summary timeline of the rapid liquid culture protocol without selection is given in Table 13.

TABLE 13

Rapid liquid culture protocol without selection.

| Days | Medium # | Culture conditions |
|---|---|---|
| 0 d | Lynx 1947 | 1 day @23° C., dark; 6 days at 30° C., dark |
| $1^{st}$ week | Lynx 2197/2379/ 2282 | 30° C., dark |
| $2^{nd}$ week | Lynx 2168 | 30° C., dark |
| $3^{rd}$ week | Lynx 2168 | 27-28° C., light |
| $4^{th}$ week | Lynx 2168 | 27-28° C., light |
| $5^{th}$ week | Lynx 1607 | Transfer explants to PHYTATRAYs |
| ~$8^{th}$ week | Transplant | Harden off plants |
| 10 days post transplanting | Sample | for glyphosate tolerance or for GUS assay or for PCT assay for GOI |
| 20 days post transplanting | Advance | Assign event numbers and advance the positive events |

To validate the above results based on the protocol described in Table 13, three experiments were conducted using transformation with pMON93040. Embryos were divided among various treatments as shown in the Table 14. In these experiments GUS assays were performed on plantlets; glyphosate was not sprayed. Embryos from each ear were isolated into a Petri-dish with 1 ml of liquid Lynx 1013 medium and co-cultured on Lynx 1947. As evident from the results, transformation using no selection is quite efficient (>60%) compared to what was achieved using selection.

TABLE 14

RAPID Transformation protocol works efficiently with both selection and no selection.

| Expt # | Treatment | # explants (IE's) | # Events | TF (%) | # Plants | Events/ 100 plants | SD | Ave plants/ IE |
|---|---|---|---|---|---|---|---|---|
| 8105-4 | RLC, Selection | 55 | 24 | 43.6 |  | N/A |  |  |
| 8106-4 |  | 80 | 34 | 42.5 |  |  |  |  |
| 8107-4 |  | 60 | 27 | 45 |  |  |  |  |
| Average |  | 195 | 85 | 43.6 |  |  |  |  |
| 8108-1 | RLC, No selection | 75 | 23 | 30.7 | 347 | 6.6 | 3.3 | 5.5 |
| 8108-2 |  | 60 | 18 | 30 | 387 | 4.7 | 3.5 | 6.5 |
| 8108-3 |  | 60 | 14 | 23.3 | 373 | 3.8 | 3.3 | 7.2 |
| Average |  | 195 | 55 | 28.2 | 369 | 5 | 3.4 | 6.4 |

In order to better understand the nature of cell proliferation and it's effect on transformation without selection, additional experiments were conducted using two different co-culture media (Lynx 1947 with 0.5 mg/l 2, 4-D and Lynx 2232 (with 0.2 mg/l 2, 4-D). Embryos from each co-culture medium were equally divided into two groups and either transferred to pre-regeneration medium (with 0.2 mg/l 2, 4-D—Lynx 2197) or regeneration medium (without any growth regulators—Lynx 2282). Five experiments (8415-8419) were conducted using a marker-less transformation vector (pMON97372) containing only the uidA gene. An outline of the experimental approach is given in FIG. 9. After establishing plants in plugs, plants from each of the embryo-derived lines were pooled and stained for GUS to identify positive lines. Later, further GUS staining of individual lines from the positive clones was performed to identify GUS positive events. About $\frac{1}{5}^{th}$ embryos from each ear were separately inoculated with a control uidA+cp4 vector (pMON97367) and the RLC protocol (e.g. Table 13) was followed to compare transformation results with and without selection (experiment 8420). The results from these experiments are summarized in Tables 15 and 16.

TABLE 15

Efficient transformation without selection using a gus vector (pMON 97372).

| Expt # | Treatment | IE size | # Explants (IEs) | # To Phytatrays | Total # plants to Plugs | # IE with Events | % TF (based on # to selection) | % TF (based on # Phytatrays) |
|---|---|---|---|---|---|---|---|---|
| 8415-1 | Co-culture on | 2.3 | 60 | 30 | 273 | 9 | 15 | 30 |
| 8416-1 | Lynx 1947 - | 2 | 60 | 37 | 273 | 9 | 15 | 24 |
| 8417-1 | 1st | 2.4 | 60 | 42 | 281 | 3 | 5 | 7.1 |
| 8418-1 | regeneration | 1.9 | 60 | 40 | 342 | 8 | 13.3 | 20 |
| 8419-1 | on Lynx 2197 | 2.1 | 60 | 37 | 405 | 7 | 11.7 | 18.9 |
|  | Total |  | 300 | 186 | 1574 | 36 | 12 | 19.4 |
| 8415-2 | Co-culture on | 2.3 | 60 | 34 | 295 | 9 | 15 | 26.5 |
| 8416-2 | Lynx 1947 - | 2 | 60 | 34 | 274 | 7 | 11.7 | 20.6 |
| 8417-2 | 1st | 2.4 | 60 | 45 | 290 | 7 | 11.7 | 15.6 |
| 8418-2 | regeneration | 1.9 | 60 | 34 | 232 | 9 | 15 | 26.5 |
| 8419-2 | on Lynx 2282 | 2.1 | 60 | 41 | 445 | 5 | 8.3 | 12.2 |
|  | Total |  | 300 | 188 | 1574 | 37 | 12.3 | 19.7 |
| 8416-3 | Co-culture on | 2 | 45 | 36 | 398 | 7 | 15.6 | 19.4 |
| 8417-3 | Lynx 2232 - | 2.4 | 45 | 28 | 239 | 3 | 6.7 | 10.7 |
| 8418-3 | 1st | 1.9 | 45 | 22 | 276 | 5 | 11.1 | 22.7 |
| 8419-3 | regeneration on Lynx 2197 | 2.1 | 40 | 37 | 256 | 4 | 10 | 10.8 |
|  | Total |  | 175 | 123 | 1169 | 37 | 10.9 | 15.4 |
| 8416-4 | Co-culture on | 2 | 45 | 28 | 297 | 2 | 4.4 | 7.1 |
| 8417-4 | Lynx 2232 - | 2.4 | 45 | 30 | 208 | 4 | 8.9 | 13.3 |
| 8418-4 | 1st | 1.9 | 45 | 33 | 226 | 4 | 8.9 | 12.1 |
| 8419-4 | regeneration on Lynx 2282 | 2.1 | 45 | 35 | 342 | 6 | 13.3 | 17.1 |
|  | Total |  | 180 | 126 | 1073 | 16 | 8.9 | 12.7 |

TABLE 16

Transformation experiments using a (pMON97367) with selection indicates transformation without selection is efficient.

| Expt # | Treatment | Control for | IE size (mm) | # to sel | # IE with Events | % TF (based on # to sel) |
|---|---|---|---|---|---|---|
| 8420-1 | Transformation | 8415 | 2.3 | 50 | 6 | 12 |
| 8420-2 | using RLC | 8416 | 2 | 40 | 5 | 12.5 |
| 8420-3 | with | 8417 | 2.4 | 40 | 4 | 10 |
| 8420-4 | pMon97367 | 8418 | 1.9 | 50 | 4 | 8 |
| 8420-5 |  | 8419 | 2.1 | 50 | 3 | 6 |
|  | Total |  |  | 230 | 22 | 9.6 |

As evident from the Table 15, co-culture medium Lynx 1947, with higher 2, 4-D concentration than Lynx 2232, was found to be superior. These results indicate that cell proliferation prior to regeneration contributes to obtaining efficient transformation without selection. Furthermore, regeneration of explants on a growth-regulator free medium (e.g. Lynx 2282) following co-culture did not appreciably reduce the number of plants/embryo. Comparison of transformation frequency with embryos that were transformed with pMON97367 using the RLC protocol demonstrates transformation without selection to be efficient. Furthermore, copy number analysis indicated a higher percentage of plants with lower copy insert (Table 17).

TABLE 17

Transformation without selection resulted in higher % of single copy, oriV negative events.

| Total # of Plants Assayed | % Single Copy Events, lacking oriV |
|---|---|
| 122 | 66 (55%) |

It is thought that the absence of selection, and/or the shorter T-DNA might be reasons for the higher % usable event production. For the no selection treatments, the preferred embryo size range is slightly larger (2.0-2.3 mm) than the embryo size range (1.9-2.1 mm) used for RLC. Validation by Southern hybridization of ~120 events (Table 17) indicated that all events are independent. This further emphasizes the earlier finding that under low TF (~15%) most of the events produced are independent events indicating that adoption of a pooling strategy prior to transplanting to growth plugs can further improve the efficiency of the protocol.

Example 10

Screening Plants Before Transplanting to Plugs to Eliminate Non-Transgenic Plants Improves Efficiency Plants from a single container containing the final growth medium (Lynx 1607) were pooled together and assayed for both gus using the histochemical GUS assay and the presence of the transgene using PCR. A 100% correlation between GUS and PCR assays was obtained. This study allowed the elimination of growth containers without positive event, thereby greatly reducing plant handling burden and improving through-put.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 5,362,865
U.S. Pat. No. 5,106,739
U.S. Pat. No. 5,107,065
U.S. Pat. No. 5,159,135
U.S. Pat. No. 5,569,834
U.S. Pat. No. 6,506,559
U.S. patent application Ser. No. 09/423,143
U.S. Patent Publn. 2002/0168707 A1
U.S. Patent Publn. 20040244075
U.S. Patent Publn. 2005/0097641
Bird et al., *Biotech Gen. Engin. Rev.*, 9:207-227, 1991.
Broothaerts et al., *Nature*, 433(7026):583-584, 2005.
Chu et al., *Scientia Sinica*, 18:659, 1975.
Darbani et al., *Biotechnol. J.*, 2:83-90, 2007.
De Vetten et al., *Nat. Biotechnol.*, 21:439-442, 2003.
Dekeyser et al., *Plant Physiol.*, 90:217-223, 1989.
Della-Cioppa et al., *Bio/Technology*, 5:579-584, 1987.
Dellaporta *Plant Mol. Biol. Rep.* 1:19-21, 1983.
Duncan et al., *Planta*, 165:322-332, 1985.
European Patent Appln. 0385 962
Francis and Spiker, *Plant J.*, 41:464-471, 2005.
Gamborg et al., *Exp. Cell Res.*, 50:151, 1968.
Gibson and Shillitoe, *Mol. Biotech.*, 7:125-137, 1997.
Goldsbrough, Methods for avoidance and removal of selectable marker genes in crop transformation systems [www.defra.gov.uk/environment/acre/uti/08.htm], 2001.
Huang et al., *Transgenic Res.* 13: 451-61, 2004.
Linsmaier and Skoog, *Physiol. Plant.*, 18: 100, 1965.
McCown and Lloyd, *HortScience*, 16:453, 1981.
Murashige and Skoog, *Physiol. Plant*, 15:473-497, 1962.
Nitsch and Nitsch, *Science*, 163:85-87, 1969.
PCT Appln. WO 09/084,942
PCT Appln. WO 09/127,735
PCT Appln. WO 2004/081184
PCT Appln. WO 97/48814
PCT Appln. WO 98/53083
PCT Appln. WO 99/53050
PCT Appln. WO 99/61631
Schenk and Hildebrandt, *Can. J. Bot.*, 50:199-204, 1972.
Uchimiya and Murashige, *Plant Physiol.* 15:473, 1962.
Yoo et al., *Planta*, 221:523-530, 2005.

What is claimed is:

1. A method for identifying transgenic corn plants, comprising:
   (a) obtaining corn plant cells transformed with a DNA segment comprising a nucleic acid sequence of interest;
   (b) regenerating a plurality of corn plants or differentiated corn plant parts from the cells without first selecting or screening for the presence of said DNA segment; and
   (c) identifying at least a first transgenic corn plant or transgenic differentiated plant part from the plurality of corn plants or differentiated corn plant parts;
   further comprising, between steps (b) and (c):
   (d) placing the plurality of corn plants or differentiated plant parts in growth plugs comprising a growth medium or water while maintaining the individual identity of the corn plants; and
   (e) subjecting the plants or plant parts to at least a first assay for the presence of the DNA segment to identify one or more plant or plant part as transgenic based on results from the assay;
   wherein individual plants, or plant parts, within the plurality of plants or differentiated plant parts of steps (d)-(e) are not labelled.

2. The method of claim 1, wherein the DNA segment does not comprise a selectable marker or visual marker gene.

3. The method of claim 1, wherein the plant cells are immature corn embryo cells.

4. The method of claim 1, wherein the assay is selected from the group consisting of Southern hybridization, PCR, DNA sequencing, northern blotting, western blotting, an immunoassay, and an assay for the enzymatic activity encoded by the DNA segment.

5. The method of claim 1, wherein the assay is performed prior to placing the regenerated plants into soil.

6. The method of claim 4, wherein putatively transformed corn plants or differentiated plant parts lacking the nucleic acid sequence of interest are identified, wherein the assay is performed on plant tissue comprising pooled subsets of nucleic acids from said plurality of corn plants or differentiated plant parts.

7. The method of claim 1, wherein the assay is performed in a microtiter plate.

8. The method of claim 1, wherein the plurality of corn plants or differentiated corn plant parts are comprised within a container holding individual plants or plant parts.

* * * * *